(12) United States Patent
Lin et al.

(10) Patent No.: US 11,535,828 B2
(45) Date of Patent: Dec. 27, 2022

(54) THREE-DIMENSIONAL TISSUE

(71) Applicant: RICOH COMPANY, LTD., Tokyo (JP)

(72) Inventors: Waka Lin, Tokyo (JP); Aino Hasegawa, Kanagawa (JP); Natsuko Hemmi, Kanagawa (JP); Satoshi Izumi, Tokyo (JP); Shusaku Shiomoto, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 219 days.

(21) Appl. No.: 16/099,360

(22) PCT Filed: May 10, 2017

(86) PCT No.: PCT/JP2017/017751
§ 371 (c)(1),
(2) Date: Nov. 6, 2018

(87) PCT Pub. No.: WO2017/199820
PCT Pub. Date: Nov. 23, 2017

(65) Prior Publication Data
US 2019/0177688 A1    Jun. 13, 2019

(30) Foreign Application Priority Data

May 20, 2016  (JP) .............................. JP2016-101177
Mar. 9, 2017   (JP) .............................. JP2017-045225

(51) Int. Cl.
| | | |
|---|---|---|
| C12N 5/00 | (2006.01) | |
| C12N 5/071 | (2010.01) | |
| C12N 5/077 | (2010.01) | |
| G01N 33/50 | (2006.01) | |
| G01N 33/58 | (2006.01) | |
| G01N 21/76 | (2006.01) | |
| C12Q 1/02 | (2006.01) | |

(52) U.S. Cl.
CPC ............. *C12N 5/069* (2013.01); *C12N 5/00* (2013.01); *C12N 5/0068* (2013.01); *C12N 5/0656* (2013.01); *C12N 5/0697* (2013.01); *C12Q 1/025* (2013.01); *G01N 21/76* (2013.01); *G01N 33/5082* (2013.01); *G01N 33/582* (2013.01); *C12N 2502/99* (2013.01); *C12N 2503/04* (2013.01); *C12N 2513/00* (2013.01)

(58) Field of Classification Search
CPC ............. C12N 5/0068; C12N 2502/99; C12N 2503/04; C12N 2513/00; C12N 5/0697; G01N 21/76; C12Q 1/025
See application file for complete search history.

(56) References Cited

U.S. PATENT DOCUMENTS

| | | | |
|---|---|---|---|
| 6,439,713 B1 | 8/2002 | Noguchi et al. | |
| 2006/0003311 A1 | 1/2006 | Fulde et al. | |
| 2007/0259328 A1 | 11/2007 | Morita et al. | |
| 2008/0113334 A1* | 5/2008 | Hattori ............... | G01N 33/5005 435/4 |
| 2009/0208466 A1 | 8/2009 | Yoo et al. | |
| 2010/0255939 A1 | 10/2010 | Mitsiades et al. | |
| 2015/0353677 A1 | 12/2015 | Izumi et al. | |
| 2016/0297927 A1 | 10/2016 | Izumi et al. | |

FOREIGN PATENT DOCUMENTS

| | | | |
|---|---|---|---|
| JP | 2002-508339 A | 3/2002 | |
| JP | 2005-342112 | 12/2005 | |
| JP | 2012-179020 | 9/2012 | |
| JP | 2015-108534 | 6/2015 | |
| JP | 2015-119643 | 7/2015 | |
| JP | 2017-163931 | 9/2017 | |
| JP | 2017-209103 | 11/2017 | |
| WO | WO2000/075286 A2 | 12/2000 | |
| WO | WO2001011340 A1 * | 2/2001 | ............. G01N 15/14 |
| WO | WO2007/124023 A2 | 11/2007 | |

OTHER PUBLICATIONS

Szot et al. In Vitro Angiogenesis Induced by Tumor-Endothelial Cell Co-Culture in Bilayered, Collagen I Hydrogel Bioengineered Tumors. Tissue Engineering: Part C vol. 19, No. 11, 2013 (Year: 2013).*
Smalley et al. In vitro three-dimensional tumor microenvironment models for anticancer drug discovery. Expert Opin. Drug Discov. (2008) 3(1):1-10(Year: 2008).*
Haddock et al. Fluorescent proteins function as a prey attractant: experimental evidence from the hydromedusa Olindias formosus and other marine organisms. Biology Open (2015) 4, 1094-1104 (Year: 2015).*
Taboada et al. Naturally occurring fluorescence in frogs. PNAS. vol. 114, No. 14. p. 3672-3677 (Year: 2017).*
le Roux et al. Optimizing Imaging of Three-Dimensional Multicellular Tumor Spheroids with Fluorescent Reporter Proteins Using Confocal Microscopy. Molecular Imaging, vol. 7, No. 5 (Sep.-Oct. 2008): pp. 214-221 (Year: 2008).*
Cote et al. Three-Dimensional Culture Assay to Explore Cancer Cell Invasiveness and Satellite Tumor Formation. J. Vis. Exp. (114), e54322, p. 1-9 (Year: 2016).*
Horie et al. Three-dimensional Co-culture Model for Tumor-stromal Interaction. J. Vis. Exp. (96), e52469. p. 1-7 (Year: 2015).*
International Search Report dated Jul. 25, 2017 for counterpart International Patent Application No. PCT/JP2017/017751 filed May 10, 2017.

(Continued)

*Primary Examiner* — Taeyoon Kim (74) *Attorney, Agent, or Firm* — Grüneberg and Myers PLLC (57) ABSTRACT

Provided is a three-dimensional tissue, including: a first cellular region including cells of a first type; and a second cellular region including cells of a second type different from the first type, wherein the cells of the first type are cells that emit light by chemiluminescence, bioluminescence, or fluorescence in response to an external stimulus.

13 Claims, 11 Drawing Sheets

(56) References Cited

OTHER PUBLICATIONS

Written Opinion dated Jul. 25, 2017 for counterpart International Patent Application No. PCT/JP2017/017751 filed May 10, 2017.
David B. Kolesky et al: "3D Bioprinting of Vascularized, Heterogeneous Cell-Laden Tissue Constructs," Advanced Materials, vol. 26, No. 19, May 1, 2014 (May 1, 2014), pp. 3124-3130, XP055303134,DE, ISSN: 0935-9648, DOI: 10.1002/adma.201305506.
Megumi Muraoka et al: "Control of the formation of vascular networks in 3D tissue engineered constructs", Biomaterials., vol. 34, No. 3, Jan. 1, 2013 (Jan. 1, 2013), pp. 696-703, XP055389820, GB, ISSN:0142-9612, DOI:10.1016/j.biomaterials.2012.10.009.
Laure Gibot et al: "Development of a tridimensional microvascularized human skin substitute to study melanoma biology", Clinical & Experimental Metastasis ; Official Journal of Themetastasis Research Society, Kluwer Academic Publishers, DO, vol. 30, No. 1, Jul. 13, 2012 (Jul. 13, 2012), pp. 83-90, XP035166326,ISSN: 1573-7276, DOI: 10.1007/s10585-012-9511-3.
Japanese Office Action dated Feb. 9, 2021 in Japanese Patent Application No. 2017-045225, 4 pages.
Office Action dated Aug. 7, 2020 in corresponding Korean Patent Application No. 10-2018-7036319 (with English Translation), 15 pages.
Japanese Office Action dated Sep. 21, 2021 in Japanese Application No. 2017-045225, with English translation, 9 pages.

\* cited by examiner

THREE-DIMENSIONAL TISSUE

TECHNICAL FIELD

The present invention relates to a three-dimensional tissue comprising cells.

BACKGROUND ART

In recent years, techniques for artificially constructing tissues formed of a plurality of cells are being developed along with the advances in stem cell research and tissue engineering.

Particularly, a major issue in evaluating safety and efficacy of, for example, medical drugs, cosmetics, and chemical substances is to develop testing methods conducted in vitro without the use of live animals (alternatives to animal testing). However, it is difficult to completely reproduce in vitro the cellular functions and drug response mechanisms as in vivo. In this regard, it is already known from studies of, for example, skin, liver, and cancer tumors that the use of three-dimensional culture is more effective for imitating physiological conditions than the use of common two-dimensional culture (monolayer culture).

As means for analyzing various phenomena occurring in cells, measuring methods using various molecular probes and bio-imaging techniques have been developed. A representative example is the reporter gene assay, which is known to allow the analysis of a gene transcription activity by photo-detecting the expression of a reporter gene introduced into the cell. Such methods for photo-detecting a response to an external stimulus are also known to be used as screening tools for, for example, drugs.

A method for evaluating the skin sensitization property of a substance has been proposed, including: a step of exposing three-dimensionally cultured skin cells to a test substance; a step of measuring the expression of at least one selected from the group consisting of specific proteins and genes encoding the specific proteins in the cells; and a step of evaluating the skin sensitization property of the test substance based on the measured expression (see, e.g., PTL 1).

Also, an in vitro model of a mammalian tissue has been proposed, containing: a three-dimensional aggregate of mammalian cells of at least two different phenotypes; and a liquid growth medium (see, e.g., PTL 2). PTL 2 also discloses a method of screening substances such as anticancer drugs that inhibit growth of cells with the use of the in vitro model of the mammalian tissue in which the cells of at least one phenotype are labeled by fluorescent staining prior to forming the three-dimensional aggregates.

CITATION LIST

Patent Literature

[PTL 1] Japanese Unexamined Patent Application Publication No. 2012-179020
[PTL 2] International Publication No. WO 2000/75286

SUMMARY OF INVENTION

Technical Problem

The object of the present invention is to provide a three-dimensional tissue that includes cells enabling the non-destructive evaluation of a response from a specific region of the three-dimensional tissue to an external stimulus.

Solution to Problem

According to one aspect of the present invention, the three-dimensional tissue includes a first cellular region including cells of a first type and a second cellular region including cells of a second type different from the first type.

The cells of the first type are cells that emit light by chemiluminescence, bioluminescence, or fluorescence in response to an external stimulus.

Advantageous Effects of Invention

The present invention can provide a three-dimensional tissue that includes cells enabling the non-destructive evaluation of a response from a specific region of the three-dimensional tissue to an external stimulus.

DESCRIPTION OF EMBODIMENTS (Three-Dimensional Tissue)

The three-dimensional tissue of the present invention includes a first cellular region including cells of a first type and a second cellular region including cells of a second type different from the first type. The cells of the first type are cells that emit light by chemiluminescence, bioluminescence, or fluorescence in response to an external stimulus (such cells may hereinafter be referred to also as "light emitting cells").

The three-dimensional tissue of the present invention is based on the following observations. The placement or distribution of cells are not controlled in the three-dimensional tissues of existing cell response evaluation systems, which only allow the measurement of an average response of a bulk of the tissue after its destruction. Therefore, with the existing systems, it is difficult to non-destructively evaluate responses from specific regions of the three-dimensional tissues, such as interactions between multiple types of cells, response variations due to changes in microenvironments in which individual cells are placed, or influences of distances from the sources of stimuli and their permeation or transmissibility.

The three-dimensional tissue is formed in vitro. A culture container, a medium, or other known materials needed for sustaining, for example, the shape, functional expression, and cell survival are appropriately used for the three-dimensional tissue depending on the intended applications.

The three-dimensional tissue is arranged to have a thickness of at least two cells in each of the three-dimensional directions.

The density of the cells is not particularly limited and may be appropriately selected depending on the intended purpose.

In the three-dimensional tissue, the cells may be directly bound with each other, or the gap between the cells may be filled with extracellular matrix (ECM) such as collagen, proteoglycan, hyaluronic acid, fibronectin, laminin, elastin, fibrillin, chitin, and cellulose, a scaffold, or a fixative described below.

The region (first cellular region) including the light emitting cells defined as the cells of the first type is a region that is identified by an abundant presence of the light emitting cells. Abundant presence means that the light emitting cells occupy 50% or greater of the volume of the region (preferably 70% or greater of the volume of the region). The detection of the light emitted from the first cellular region makes it possible to distinguish the first cellular region from a region in which the light emitting cells are absent and to define the boundary of the region that is the target of the stimulus-response evaluation.

The region (second cellular region) including cells (cells of a second type) different from the light emitting cells is a region identified by the absence of the light emitting cells. It is preferable that the region including the light emitting cells and the region including the cells different from the light emitting cells be adjacent to each other. However, a region in which the light emitting cells are present dispersedly in a small amount (less than 50% of the volume) may be present between the two regions.

The external stimulus is not particularly limited and may be appropriately selected depending on the intended purpose. Examples of the external stimulus include exposure to and introduction of a stimulating substance, physical changes such as temperature and pressure changes, exposure to stressors such as hypoxic conditions, oxidation conditions, or ultraviolet irradiation, changes of culture conditions, and factors that bring significant changes to the micro-environments surrounding the cells such as contact with the culture container or scaffold materials.

There is a possibility that cells present at a specific position in the three-dimensional tissue may respond to the external stimulus in a different manner from how cells present in another region respond to the external stimulus due to, for example, the difference in the structure of the surrounding tissue or the distance from the source of the stimulus. For example, when the external stimulus is applied to the three-dimensional tissue from a certain direction, there is a possibility that the degree of stimulation, i.e., the reaction of the cells may vary depending on the distance on an axis perpendicular to the interface to which the stimulus is applied. Hence, it is preferable that the region including the light emitting cells be arranged at a distance suitable for enabling the evaluation of the variation.

The three-dimensional tissue can be used for evaluation of safety or efficacy of a stimulating substance or for drug screening. Furthermore, for pharmacokinetic studies or development of regenerative medicine, the three-dimensional tissue may be transplanted in a living animal to observe the process of tissue or organ regeneration.

Figure 1A:
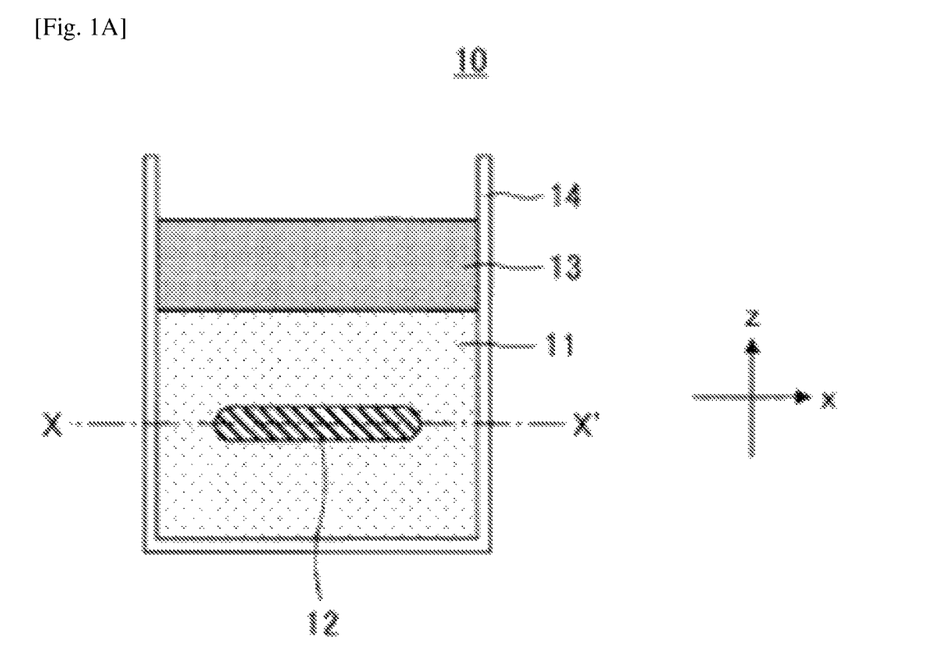
FIG. 1A is a schematic cross-sectional view illustrating an example of the overall configuration of a three-dimensional tissue of the present invention, the cross-sectional view being taken in a vertical direction.
Figure 1B:
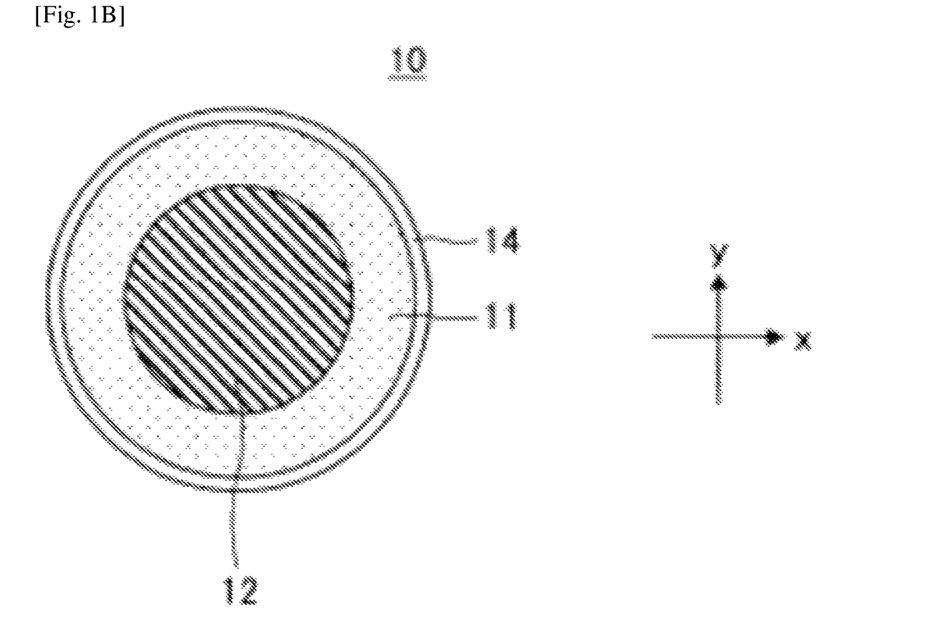
FIG. 1B is a schematic cross-sectional view illustrating an example of the overall configuration of a three-dimensional tissue of the present invention, the cross-sectional view being taken in a horizontal direction.

FIG. 1A and FIG. 1B illustrate an example of the overall configuration of the three-dimensional tissue of the present invention. FIG. 1A is a schematic cross-sectional view taken in a vertical direction in an xz plane. FIG. 1B is a schematic cross-sectional view taken in a horizontal direction along an X-X' direction of FIG. 1A (in an xy plane).

The three-dimensional tissue 10 is composed of a region 11 including cells A, a region 12 including cells B, and a medium 13 stacked sequentially in a culture container 14.

The cells B defined as the cells of the first type are light emitting cells.

The cells A defined as the cells of the second type may be light emitting cells different from the cells B or may not be light emitting.

It is preferable that the surface of the region 12 including the cells B be not in contact with the circumferential wall of the culture container 14 in order to avoid artifacts due to the presence of the culture container. Specifically, it is preferable that the region 12 including the cells B be arranged in the center of the three-dimensional tissue 10. This makes it possible to eliminate interfacial influences between the region 12 including the cells B and the culture container 14.

It is preferable that relatively to the total region comprising both the region including the cells B (first cellular region) and the region including the cells A (second cellular region), the proportion of the first cellular region be smaller than the proportion of the second cellular region, and that the volume ratio of the first cellular region to the total be less than 0.5 and more preferably no greater than 0.3. In this way, the region including the cells B is restricted and can be evaluated separately from the whole tissue.

It is preferable that the region 12 including the cells B be present at a certain distance on an axis perpendicular to an interface to which a stimulus is applied. This makes it possible to evaluate the influence of the distance from the source of the stimulus or permeability of the stimulating substance.

The three-dimensional tissue only requires that a region including the cells B be present in the region including the cells A, and the region including the cells B does not need to have a layer form.

The three-dimensional tissue may further include a region including cells different from the cells A and the cells B. In this case, the cells different from the cells A and the cells B may or may not be light emitting cells.

<Method for Arranging Cells A and B>

The method for arranging the cells is not particularly limited and a known method may be appropriately used. Examples of the method include pipette dispensing, micromanipulator, inkjet technology, gel extrusion technology, transfer methods such as screen printing, and optical tweezer. Among these methods, the inkjet technology is preferable in terms of efficiently arranging the cells in a narrow region of from some tens of square micrometers through some square millimeters thinly and uniformly. The inkjet technology can arrange 1 through 10 cells accurately because the inkjet technology allows the ejection of liquid droplets of a few picoliters.

<Cells A and B>

The cells A and B are not particularly limited so long as the cells A and B can form the three-dimensional tissue. Any types of cells such as eukaryotic cells, prokaryotic cells, cells of multicellular organisms, and cells of unicellular organisms may be used. Among these cells, adherent cells derived from mammals or humans and having a cell adhesiveness of a level such that the cells are not isolated without physicochemical treatment are preferable.

<Light Emitting Cells>

The light emitting cells emit light by chemiluminescence, bioluminescence, or fluorescence. This makes it possible to analyze various molecular mechanisms that occur in the cells in response to an external stimulus.

Chemiluminescence is a light emission phenomenon accompanying a chemical reaction. Examples of chemiluminescence include the luminol reaction that occurs when peroxidase decomposes hydrogen peroxide.

Bioluminescence is a chemiluminescence emitted by a living organism and refers to a phenomenon that an energy is emitted in the form of light in response to an action of, for example, a luciferase. Examples of bioluminescence include the emission of light that occurs when firefly luciferase (enzyme) oxidizes luciferin (substrate).

Fluorescence is light emitted along with electron transition when a substance in an excited state returns to the ground state. Examples of fluorescence by living organisms include the emission of green light that occurs when the green fluorescent protein (GFP) from the jellyfish *Aequorea victoria* is exposed to the appropriate excitation light.

It is preferable that a reporter gene be introduced into the light emitting cells. This makes it possible to measure the expression level based on the transcription activity of a target gene that is to be monitored for the response.

In this case, the reporter gene is linked downstream of a promoter of the target gene that is to be measured for the expression level.

The reporter gene is not particularly limited and may be appropriately selected depending on the intended purpose. Examples of the reporter gene include luciferase gene, green fluorescent protein (GFP) gene, and derivatives of these genes.

As for the light emitting cells, mammalian cells transformed with a luciferase gene are preferable because they allow a quantitative measurement of gene transcription activity and its stable monitoring for a long time. For example, the method of introducing an artificial chromosome vector containing a luciferase gene construct, as disclosed in Japanese Unexamined Patent Application Publication No. 2015-119643, may be used.

Examples of other methods for making cells emit light include, but are not particularly limited to, known methods such as fluorescence/bioluminescence resonance energy transfer (FRET/BRET) for evaluating interactions between various intracellular molecules, and introduction of a fluorescent/luminescent substrate to serve as an indicator of activity or migration of, for example, enzymes or binding factors (e.g., fluorescent calcium indicators, Aldefluor assay, glucose uptake imaging, and fluorescent nanoparticle probes).

When the cells A and the cells B are both light emitting cells, the cells A and the cells B can be distinguished from each other with the use of, for example, light emitting cells that emit light under different conditions or at different timings, or light emitting cells that emit light of different wavelengths. For example, light emitting cells that emit light of different wavelengths may be arranged at different depths in the three-dimensional tissue. Furthermore, diseased cells and normal cells that emit light under different conditions may be arranged for co-culture, and reactions of these types of cells may be compared with each other.

<Culture Container>

The culture container is formed of materials to serve as a base or a support needed for forming and maintaining the three-dimensional tissue.

The constituent of the base material is not particularly limited and may be appropriately selected depending on the intended purpose. Examples of the constituent of the base materials include resins, glass, and metals.

The structure of the base material is not particularly limited and may be appropriately selected depending on the intended purpose. Examples of the structure of the base material include planar structures, porous or spongiform structures, meshes, structures with rough or patterned topography, and honeycombs.

It is preferable to use as culture container, a multi-well type culture plate or insert that is formed of a base material suitable for adhesion and proliferation of cells, has a high optical transparency, and does not self-luminesce.

In the three-dimensional tissue 10, the region 11 including the cells A is in contact with the culture container 14. However, the region 11 including the cells A does not need to be constantly in contact with the culture container 14. Furthermore, the three-dimensional tissue 10 is an open system in order to let in or out the medium 13, the substance that is to be evaluated for safety or efficacy, or the drugs to be screened. However, the three-dimensional tissue 10 may be a closed system allowing perfusion culture, or may be a chip type including microfluidics.

<Medium>

The medium is a solution that contains components needed for forming and maintaining the three-dimensional tissue, prevents drying, and conditions the external environment such as osmotic pressure.

The medium is not particularly limited and may be appropriately selected from known media depending on the intended purpose.

When the three-dimensional tissue does not need to be constantly submerged in the medium such as when the three-dimensional tissue is air-lifted skin, the medium may be removed appropriately.

<Fixative>

A fixative may be needed in some cases in order to fix the cells B at a specific position to maintain the structure of the three-dimensional tissue. The time for which the cells B are fixed may be temporary or permanent, but needs to be a time that at least ensures that the three-dimensional tissue will not collapse during cell culture and during use. A fixative that has biocompatibility and does not adversely affect the cells is preferable. The fixative may be mixed with the cells, or may be deposited separately from the cells.

The fixative is not particularly limited and may be appropriately selected depending on the intended purpose. Examples of fixative include biopolymers (e.g., collagen, elastin, gelatin, and fibroin), coagulation factors (e.g., fibrinogen/thrombin), adhesion factors (e.g., fibronectin, laminin, and recombinant peptide), synthetic polymers such as polylactic acid, and polysaccharides/polyvalent metal salts such as alginic acid and gellan gum.

Depending on the method for arranging the cells, it may be preferable that the fixative be a phase-change material that thickens in response to mixing of two or more liquids.

When the phase-change material that thickens in response to mixing of two or more liquids is used as the fixative, one of the liquids may be previously mixed with the cell suspension, or liquid droplets may be deposited at suitable positions separately. When the fixative is used, the fixative may or may not remain in the three-dimensional tissue.

EXAMPLES

The present invention will be described below by way of Examples. However, the present invention should not be construed as being limited to these Examples.

Example 1

—Preparation of Cells—

As cells A, normal human dermal fibroblasts (available from Lonza Japan, Ltd.) (hereinafter referred to as "NHDF cells") were used.

As cells B, commercially available mouse fibroblasts NFkB-luciferase NIH3T3 Reporter Stable Cell Line (available from Panomics Inc.) including a luciferase genetic sequence linked downstream of the promotor of a responsive element to the NF-κB transcription factor (hereinafter referred to as "NFkB-luc cells") were used. First, the NHDF cells and the NFkB-luc cells were pre-cultured according to the procedures recommended by the manufacturers.

Next, after the cells were isolated by trypsinization, the NHDF cells and the NFkB-luc cells were stained with CellTracker Green and CellTracker Orange (both available from Thermo Fisher Scientific Inc.) respectively in order for the cells to be distinguishable by confocal fluorescence microscopy independently from their light emitting reaction.

—Production of Three-Dimensional Tissue—

As illustrated in FIG. 2A to FIG. 2E, a three-dimensional tissue was produced using the stained NFkB-luc cells and NHDF cells.

Figure 2A:
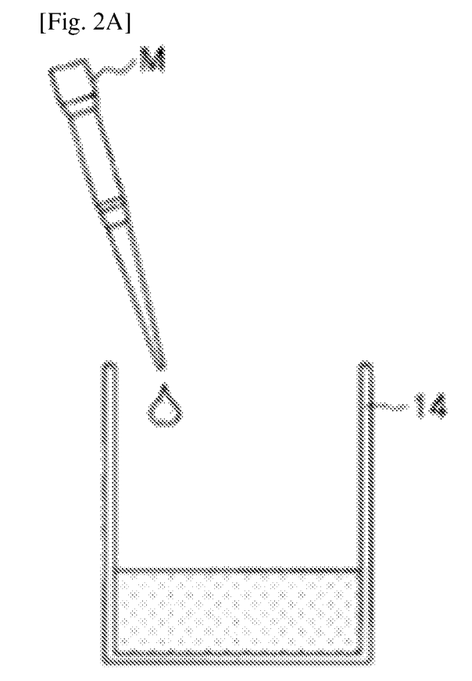
FIG. 2A is a view illustrating an example of a method for producing the three-dimensional tissue of Example 1, depicting a state that NHDF cells are dispensed into a culture container with a micropipette.
Figure 2B:
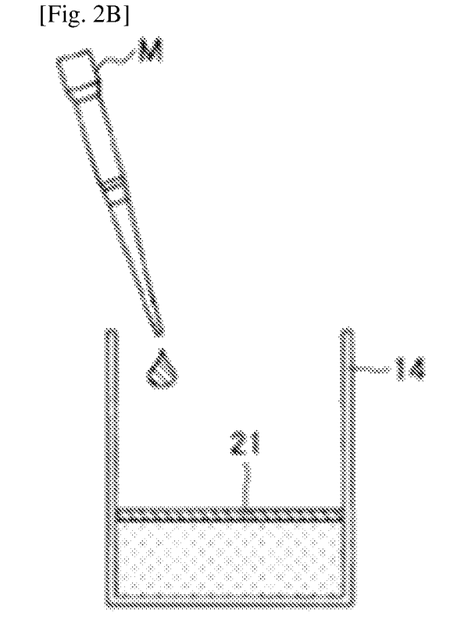
FIG. 2B is a view illustrating an example of a method for producing the three-dimensional tissue of Example 1, depicting a state that a fixative factor is added with a micropipette to form a thin film in order to immobilize the NFkB-luc cells to be arranged.

First, 20 microliters of NHDF cells suspended in a 0.2% (w/v) collagen solution at a density of $1\times10^7$ cells/mL were dispensed into a well (0.3 cm$^2$) of a 96-well plate, defined as the culture container 14, with a micropipette M, and left to stand still in a $CO_2$ incubator at 37 degrees C. until the cell layer was solidified (see FIG. 2A).

Next, in order to fix the NFkB-luc cells to be arranged, a few microliters of a 25 mg/mL aqueous solution of fibrinogen, defined as the fixative factor 21, was added with the micropipette M. Then, the supernatant was removed so that only a thin film remained (see FIG. 2B).

Figure 2C:
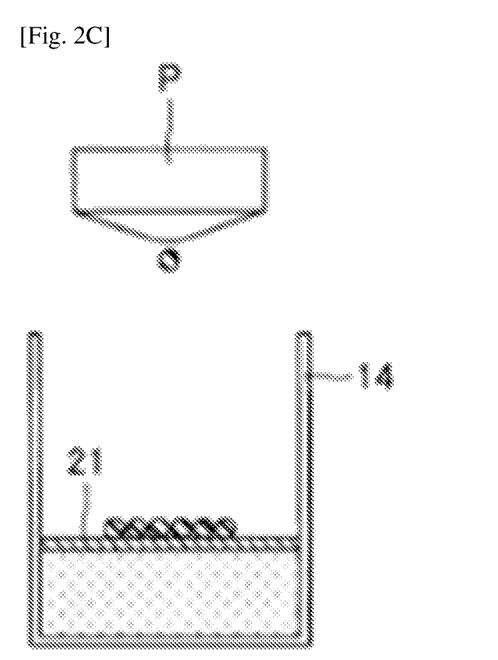
FIG. 2C is a view illustrating an example of a method for producing the three-dimensional tissue of Example 1, depicting a state that NFkB-luc cells are ejected from an inkjet bioprinter P in a manner that the cells are arranged into a layer, the thickness of which is of the height of a single cell.

Next, NFkB-luc cells suspended in a DMEM medium containing 20 U/mL of thrombin, which was a coagulation factor, were ejected at a density of about 100 cells/mm$^2$ from an inkjet bioprinter P (a prototype of an inkjet bioprinter developed in-house) configured to eject a liquid droplet including 1 to 10 cells per some tens of picoliters, in a manner that the NFkB-luc cells would be arranged into a layer having a thickness corresponding to one NFkB-luc cell (see FIG. 2C).

Figure 2D:
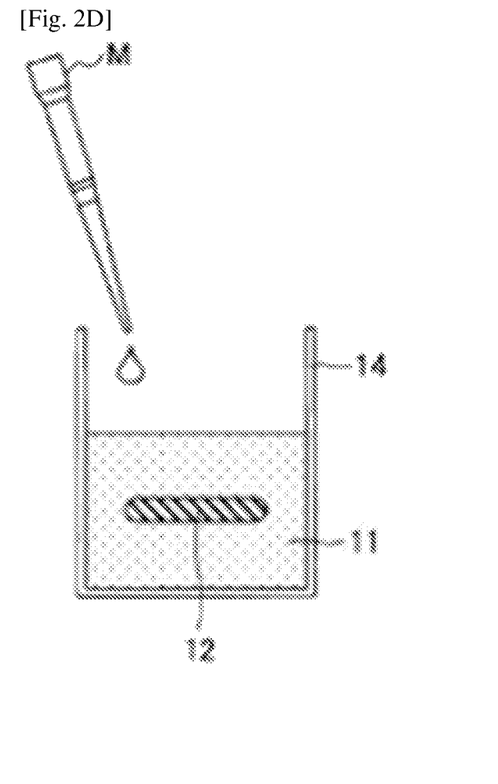
FIG. 2D is a view illustrating an example of a method for producing the three-dimensional tissue of Example 1, depicting a state that NHDF cells suspended in a collagen solution are added onto a layer of NFkB-luc cells with a micropipette M and left to stand still until the cell layer is solidified.

Next, 20 microliters of NHDF cells suspended in a 0.2% (w/v) collagen solution at a density of $1\times10^7$ cells/mL were added onto the layer of the NFkB-luc cells with the micropipette M, and left to stand still in a $CO_2$ incubator at 37 degrees C. until the cell layer was solidified (see FIG. 2D).

Figure 2E:
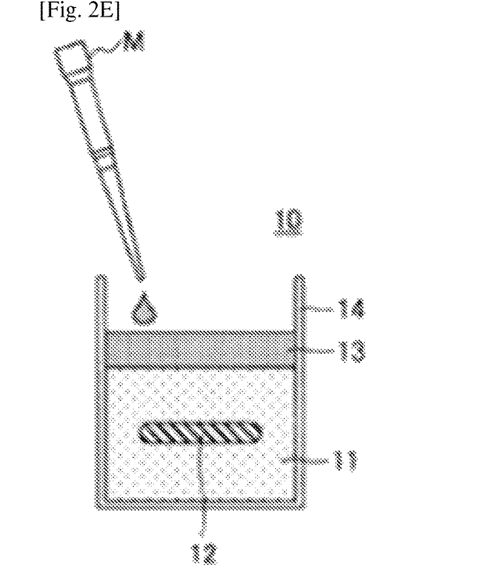
FIG. 2E is a view illustrating an example of a method for producing the three-dimensional tissue of Example 1, depicting a state that a DMEM medium is added to produce a three-dimensional tissue by culturing.

Next, 100 microliters of DMEM medium, defined as the medium 13, was added with the micropipette M, and left to stand still overnight in a $CO_2$ incubator at 37 degrees C., to obtain the three-dimensional tissue 10 (see FIG. 2E).

Next, the produced three-dimensional tissue 10 was observed with a confocal fluorescence microscope FV10i-LIV (available from Olympus Corporation).

Figure 3:
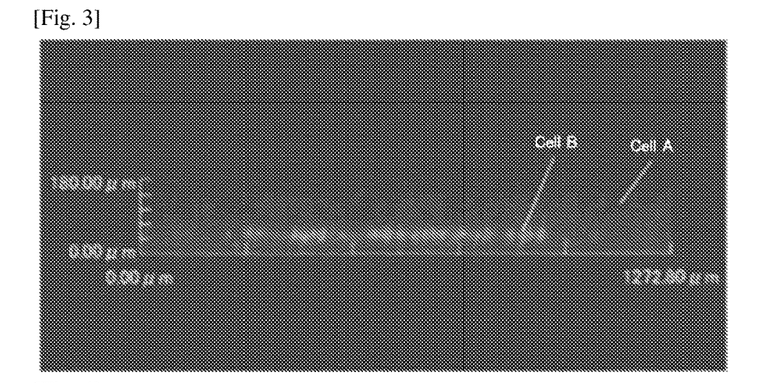
FIG. 3 is a microscopic Z-stack image illustrating an example of the three-dimensional tissue of Example 1.

FIG. 3 illustrates a Z-stack captured image of the three-dimensional tissue 10. From FIG. 3, it was confirmed that the region 12 including the cells B (NFkB-luc cells) having a color different from the cells A (NHDF cells) was arranged to have a thickness corresponding to one cell B (NFkB-luc cell) in the center of a region 11 including the cells A (NHDF cells) and having a thickness of about 180 micrometers.

Example 2

Figure 4:
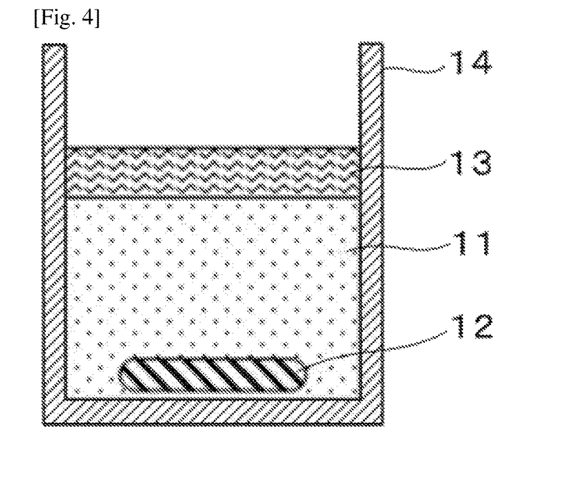
FIG. 4 is a cross-sectional view illustrating an example of the overall configuration of the three-dimensional tissue of Example 2.

A three-dimensional tissue was obtained in the same manner as in Example 1, except that unlike Example 1, the region 12 including the cells B (NFkB-luc cells) was arranged in the bottom portion of a region 11 including the cells A (NHDF cells) and having a thickness of 1.6 mm (see FIG. 4).

Example 3

Figure 5:
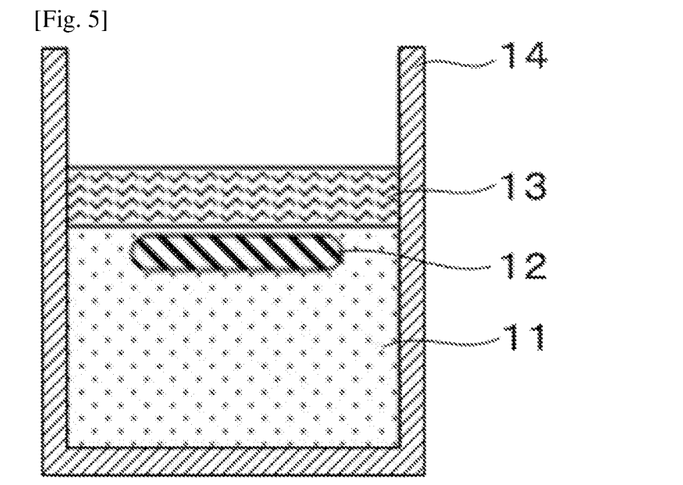
FIG. 5 is a cross-sectional view illustrating an example of the overall configuration of the three-dimensional tissue of Example 3.

A three-dimensional tissue was obtained in the same manner as in Example 1, except that unlike Example 1, the region 12 including the cells B (NFkB-luc cells) was arranged in the top portion of a region 11 including the cells A (NHDF cells) and having a thickness of 1.6 mm (see FIG. 5).

Control Example 1

Figure 6:
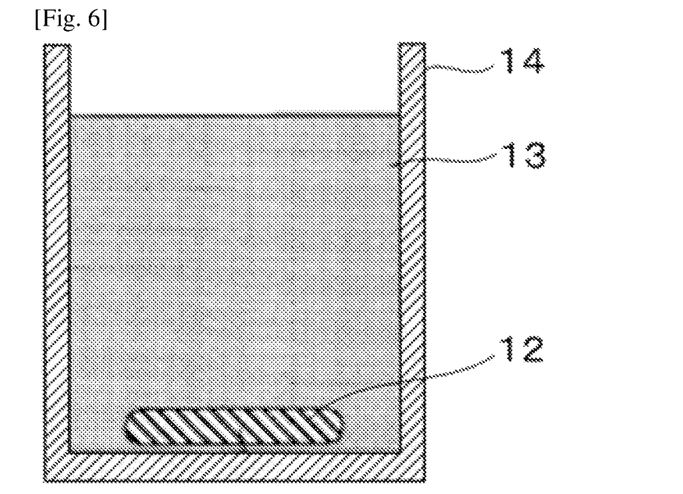
FIG. 6 is a cross-sectional view illustrating an example of the overall configuration of the three-dimensional tissue of Control Example 1.

A three-dimensional tissue was obtained in the same manner as in Example 2, except that unlike Example 2, a DMEM medium was dispensed instead of a region 11 including the cells A (NHDF cells) (see FIG. 6).

Comparative Example 1

Figure 7:
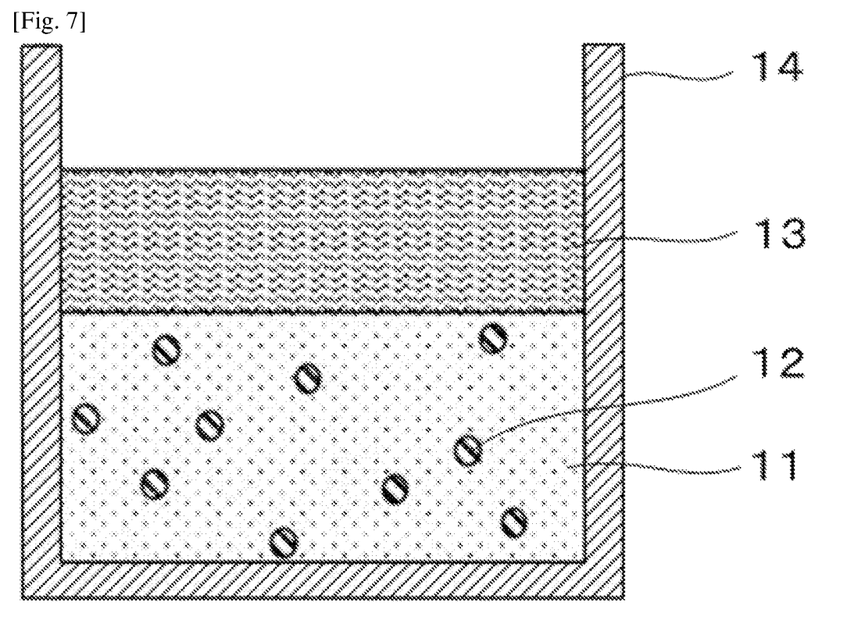
FIG. 7 is a schematic cross-sectional view illustrating an example of the overall configuration of the three-dimensional tissue of Comparative Example 1.

FIG. 7 illustrates a three-dimensional tissue of Comparative Example 1.

When no light emitting cells for enabling identification of the observation region were included as in the "3D-cultured skin model Epiderm™ (available from MatTek Corporation)" used in Examples 1 and 2 of Japanese Unexamined Patent Application Publication No. 2012-179020, or when light emitting cells were included but were dispersed randomly in the entire volume of the three-dimensional tissue as illustrated in FIG. 7, it would be possible to measure only average responses from the entire volume of the three-dimensional tissue as a bulk, and there would be a need to employ a technique of arranging light emitting cells in a target region in order to nondestructively evaluate whether a specific region in the three-dimensional tissue would react differently from another region.

Comparative Example 2

Figure 8:
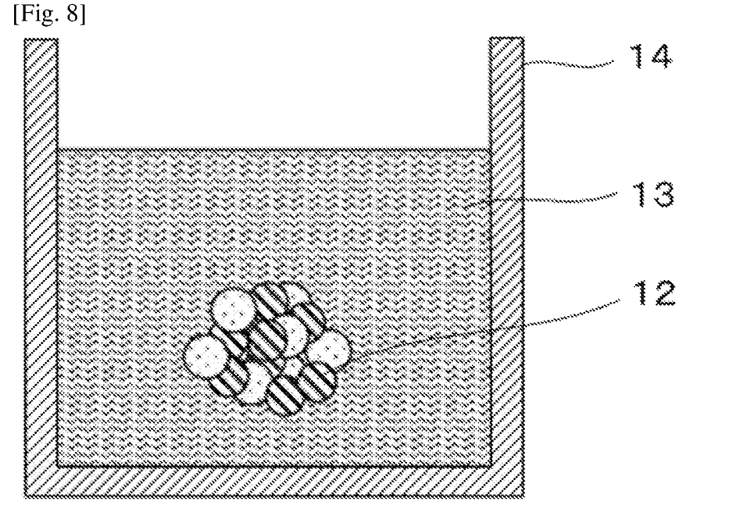
FIG. 8 is a schematic cross-sectional view illustrating an example of the overall configuration of the three-dimensional tissue of Comparative Example 2.

FIG. 8 illustrates a three-dimensional tissue of Comparative Example 2 reproducing Example 2 (FIG. 3) of International Publication No. WO 2000/75286.

When light emitting cells and other cells were mixed overall as illustrated in FIG. 8, it would be possible to measure only average responses from the entire volume of the three-dimensional tissue as a bulk, and there would be a need to employ a technique of arranging light emitting cells in a region of interest in order to non-destructively evaluate whether a specific region in the three-dimensional tissue would react differently from another region.

Figure 9A:
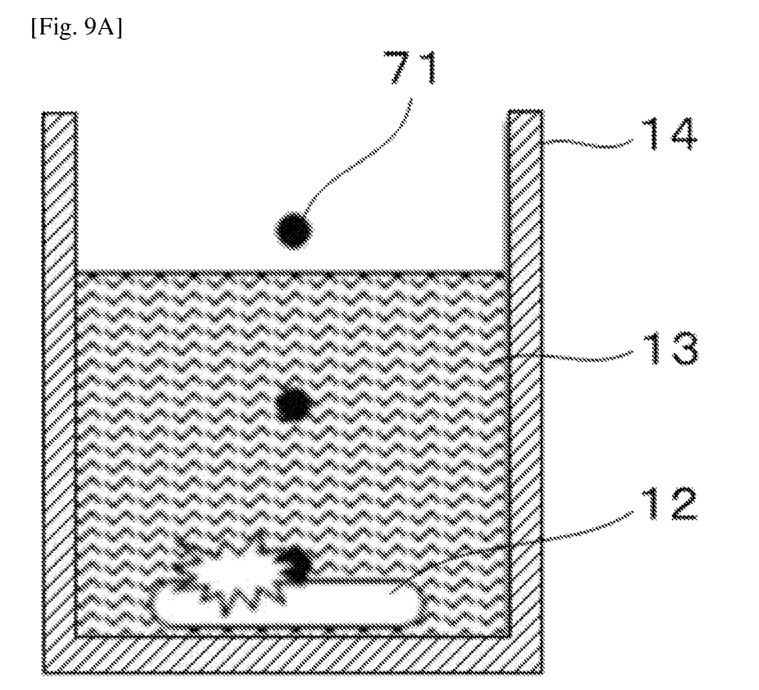
FIG. 9A is a view illustrating a state of the three-dimensional tissue of Control Example 1 during measurement of light emission intensity.
Figure 9B:
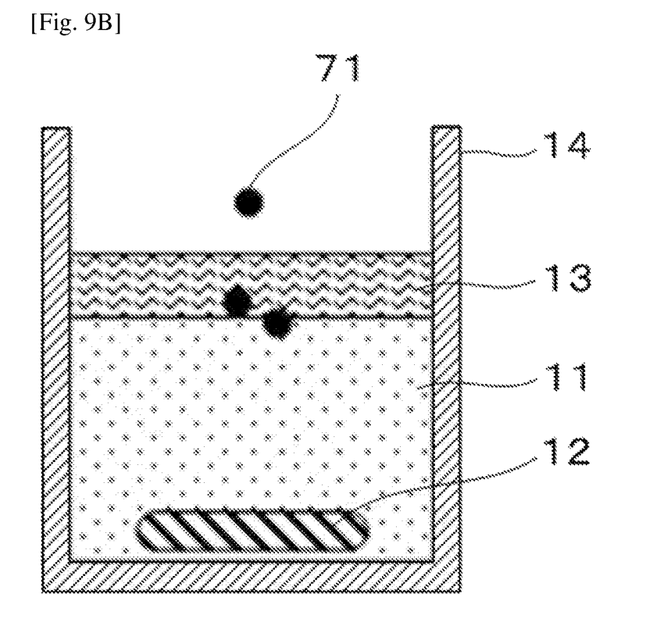
FIG. 9B is a view illustrating a state of the three-dimensional tissue of Example 2 during measurement of light emission intensity.
Figure 9C:
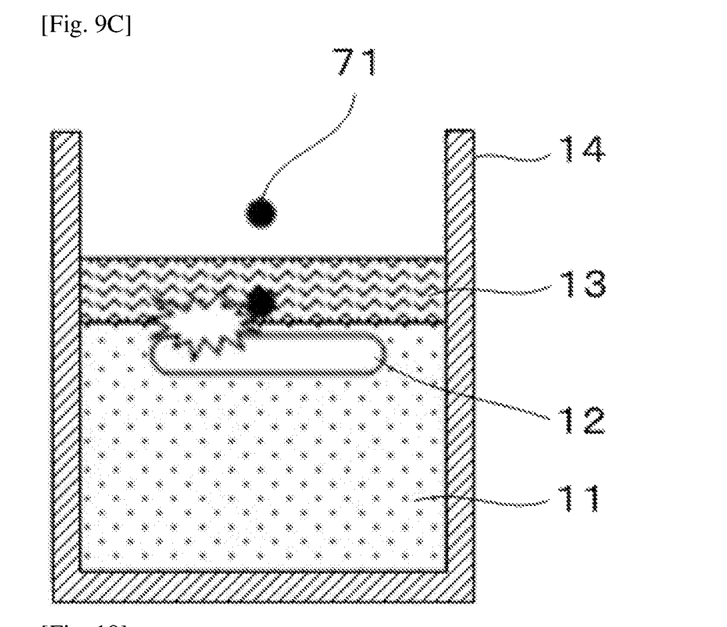
FIG. 9C is a view illustrating a state of the three-dimensional tissue of Example 3 during measurement of light emission intensity.

Next, emission intensities of the three-dimensional tissues of Example 2, Example 3, and Control Example 1 were measured. FIG. 9A illustrates a state of the three-dimensional tissue of Control Example 1 during measurement of the emission intensity. FIG. 9B illustrates a state of the three-dimensional tissue of Example 2 during measurement of the emission intensity. FIG. 9C illustrates a state of the three-dimensional tissue of Example 3 during measurement of the emission intensity.

<Emission Intensity>

In order to induce the luminescence of the NFkB-luc cells, a 50 ng/mL aqueous solution of TNF-α, defined as the stimulating substance 71, and a 200 μM aqueous solution of D-luciferin, which was a luminescent substrate, were added to the three-dimensional tissues, which were then left to stand still in a $CO_2$ incubator at 37 degrees C. for 4 hours. Next, with a plate reader Cytation 5 (available from BioTek Instruments Inc.) set to a gain of 175 and an integral time of 3 seconds, the emission intensities of the three-dimensional tissues (8 samples of each) were measured.

Here, a DMEM medium was used as a blank. Table 1 presents the measurements of the emission intensities of the three-dimensional tissues.

TABLE 1

| Blank | Control Example 1 | Example 2 | Example 3 |
|---|---|---|---|
| 99 | 6,713 | 412 | 6,974 |
| 104 | 6,455 | 123 | 5,976 |
| 141 | 6,647 | 214 | 6,423 |
| 111 | 6,157 | 251 | 5,150 |
| 121 | 6,158 | 208 | 5,523 |
| 101 | 5,971 | 356 | 5,813 |
| 113 | 6,174 | 357 | 5,533 |
| 98 | 5,966 | 290 | 5,569 |

Next, the emission intensities of the blank were subtracted from the emission intensities of the three-dimensional tissues, and then the average emission intensities and standard deviations were calculated.

Figure 10:
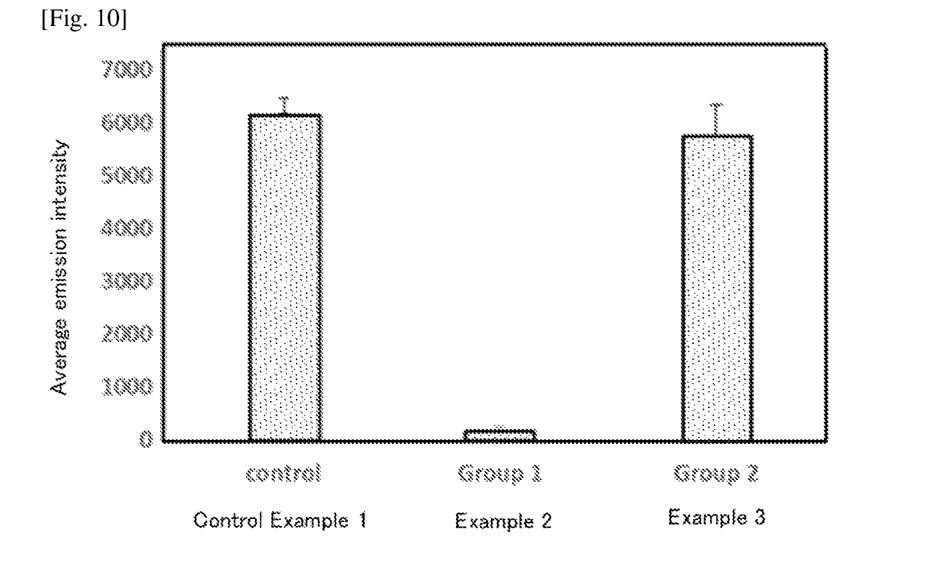
FIG. 10 is a graph plotting the average emission intensities and the standard deviations of Example 2, Example 3, and Control Example 1.

FIG. 10 plots the average emission intensities and the standard deviations of Example 2, Example 3, and Control Example 1.

FIG. 9A and FIG. 10 concern Control Example 1.

From FIG. 9C and FIG. 10, it was revealed that an emission intensity comparable to the emission intensity of Control Example 1 was detected from the three-dimensional tissue of Example 3 in response to the stimulating substance (TNF-α) 71 added from the top, because in Example 3, the region 12 including the cells B (NFkB-luc cells) was arranged in the top portion of the region 11 including the cells A (NHDF cells).

On the other hand, from FIG. 9B and FIG. 10, it is seen that the emission intensity of the three-dimensional tissue of Example 2 was low, because in Example 2, the region 12 including the cells B (NFkB-luc cells) was arranged in the bottom portion of the region 11 including the cells A (NHDF cells). From this result, it was suggested that the stimulating substance (TNF-α) 71 had not permeated the region 12 including the cells B (NFkB-luc cells) due to the influence of the thickness of the region 11 including the cells A (NHDF cells).

It was possible to exclude the possibility that the low emission intensity was simply because the light was absorbed by the region 11 including the cells A (NHDF cells), by using cells that would emit light independently from the stimulating substance instead of the cells B (NFkB-luc cells) (e.g., TK-Luc cells including a luciferase genetic sequence linked downstream of a constitutively expressed thymidine kinase promotor). These results indicate that non-destructive evaluation of the emission intensity, i.e., a response to the stimulating substance from a specific region was possible with the three-dimensional tissues of Example 2 and Example 3. Further, by comparing Example 2 and Example 3 with each other, it was possible to evaluate whether the response to the stimulating substance would vary depending on the position of the region in the three-dimensional tissue.

Example 4

Figure 11A:
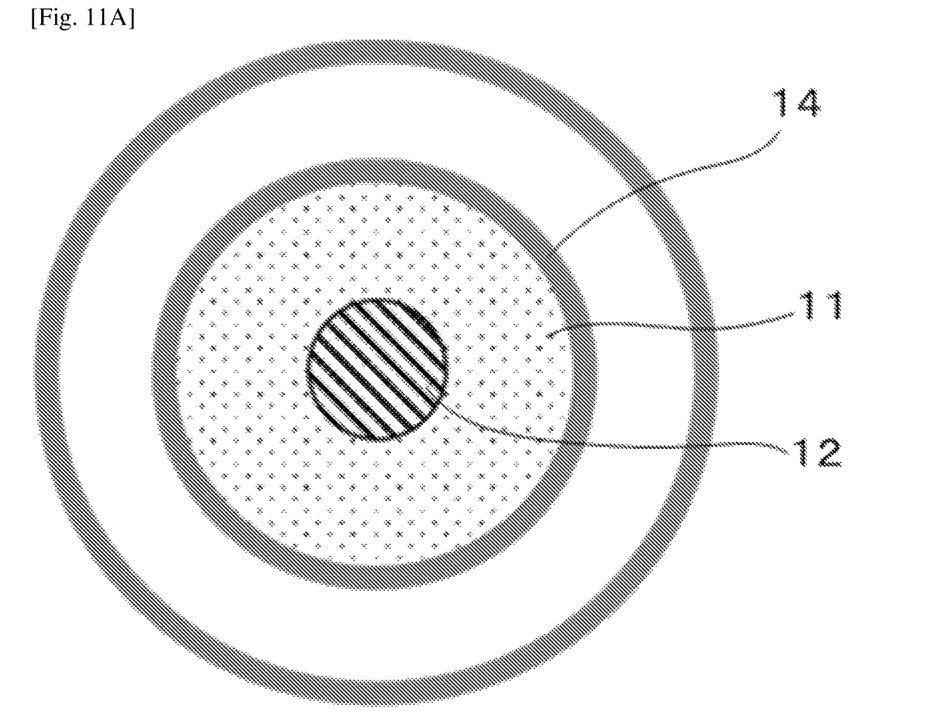
FIG. 11A is a schematic cross-sectional view illustrating an example of the overall configuration of the three-dimensional tissue of Example 4, the cross-sectional view being taken in a horizontal direction.
Figure 11B:
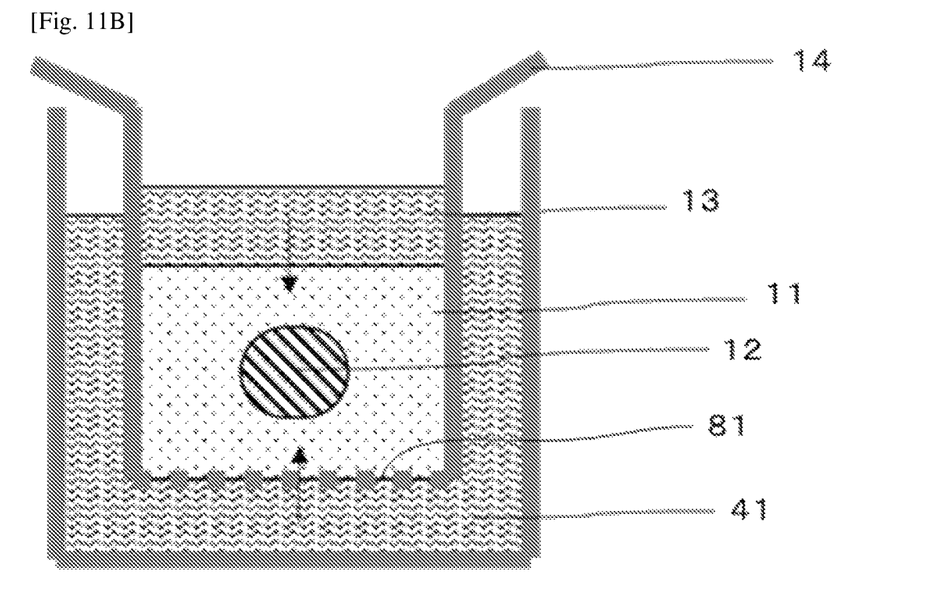
FIG. 11B is a schematic cross-sectional view illustrating an example of the overall configuration of the three-dimensional tissue of Example 4, the cross-sectional view being taken in a vertical direction.

There is no need for the shape of the region 12 including the cells B to be a layer. In the examples illustrated in FIG.

11A and FIG. 11B, a spherical aggregate (spheroid) formed of the cells B (NFkB-luc cells) and having a diameter of about 300 micrometers was prepared using a low adsorption culture plate (available from Sumitomo Bakelite Co., Ltd.).

Next, the cells A (NHDF cells) suspended in a 0.2% (w/v) collagen solution were arranged in the culture container 14 in the same manner as in Example 1. Here, a Falcon culture insert having a size of 0.4 micrometers (available from Corning Incorporated) was used as the culture container 14 instead of a culture plate to which a stimulating substance could be added from only the top. With this culture container, it was possible to immerse the entire three-dimensional tissue in the culture medium and in the stimulating substance from also the bottom 81 (see FIG. 11B) formed of a porous membrane.

Finally, the spheroid of the cells B (NFkB-luc cells) was arranged in the center of the region 11 including the cells A (NHDF cells) with a micro-manipulator, and the cells A suspended in a 0.2% (w/v) collagen solution were further added in a manner that the spheroid would be completely embedded. When Example 4 was used, it was possible to evaluate the emission intensity at the central region i.e., in response to a stimulus penetrating from the exterior to the interior of the three-dimensional tissue.

Further, when the container of this form was used, including different stimulating substances in the medium 13 at the top and the culture medium 41 at the bottom was possible. Therefore, for example, it was possible to evaluate a response that would occur only when two different stimulating substances reached simultaneously the central region 12 including the cells B.

Example 5

Figure 12A:
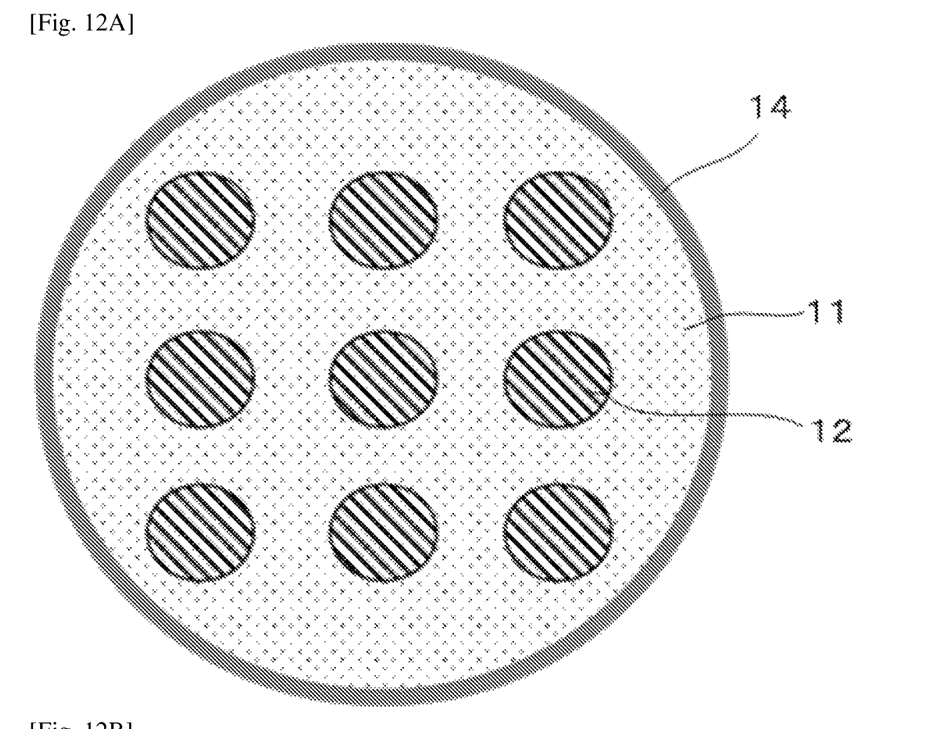
FIG. 12A is a schematic cross-sectional view illustrating an example of the overall configuration of the three-dimensional tissue of Example 5, the cross-sectional view being taken in a horizontal direction.
Figure 12B:
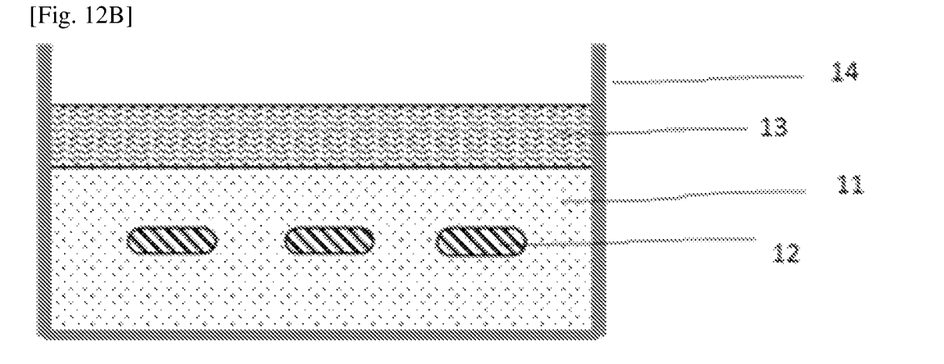
FIG. 12B is a schematic cross-sectional view illustrating an example of the overall configuration of the three-dimensional tissue of Example 5, the cross-sectional view being taken in a vertical direction.

The region 12 including the cells B does not need to be uniform, but multiple regions including the cells B may be arranged in the same three-dimensional tissue at specific X, Y, and Z coordinates as illustrated in FIG. 12A and FIG. 12B. The three-dimensional tissue of Example 5 was produced in the same manner as in Example 1, except that using the same inkjet bioprinter P as used in Example 1, regions 12 including the cells B (NFkB-luc cells) were arranged at nine isolated areas at previously set coordinates in the culture container 14, which was a culture dish having a size of 3.5 mm.

When Example 5 was used, it was possible to evaluate not only permeation of the stimulating substance in the depth direction, but also the reaction transmission speed in a wide range.

Example 6

Figure 13:
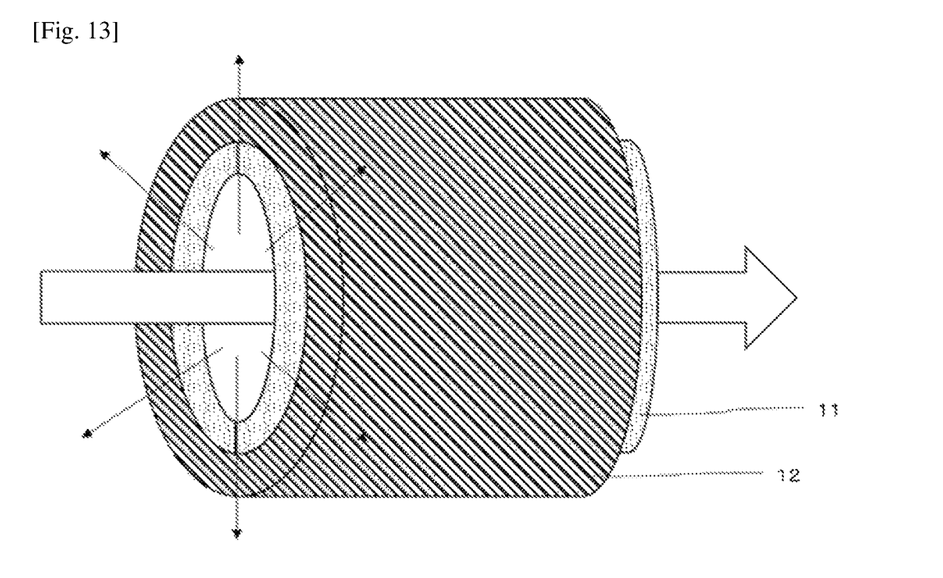
FIG. 13 is a schematic cross-sectional view illustrating an example of the overall configuration of the three-dimensional tissue of Example 6.

The region 12 including the cells B may have a form enclosing the region 11 including the cells A, as illustrated in FIG. 13. With the same inkjet bioprinter P as used in Example 1, a cell sheet including the cells A and a cell sheet including the cells B were previously constructed and stacked in the form of a two-layered structure. The obtained product was rolled into a tubular shape, and perfused on the inside for culture. In this case, it was possible to evaluate whether a response to the stimulus would vary radially from the inside of the tube toward the outside.

Aspects of the present invention are as follows, for example.

<1> A three-dimensional tissue, including:
a first cellular region including cells of a first type; and
a second cellular region including cells of a second type different from the first type,
wherein the cells of the first type are cells that emit light by chemiluminescence, bioluminescence, or fluorescence in response to an external stimulus.
<2> The three-dimensional tissue according to <1>,
wherein the cells of the first type are absent in the second cellular region, and
wherein the cells of the first type are present abundantly in the first cellular region.
<3> The three-dimensional tissue according to <1> to <2>,
wherein relatively to the total region comprising both the first cellular region and the second cellular region, the proportion of the first cellular region is smaller than the proportion of the second cellular region.
<4> The three-dimensional tissue according to any one of <1> to <3>,
wherein a surface of the first cellular region is present at a certain distance on an axis perpendicular to an interface to which a stimulus is applied.
<5> The three-dimensional tissue according to any one of <1> to <4>,
wherein the first cellular region and the second cellular region are arranged inside a culture container.
<6> The three-dimensional tissue according to <5>,
wherein the first cellular region is not in contact with a circumferential wall of the culture container.
<7> The three-dimensional tissue according to any one of <1> to <6>,
wherein a reporter gene is introduced into the cells of the first type.
<8> The three-dimensional tissue according to any one of <1> to <7>,
wherein the cells of the second type are not cells that emit light.
<9> The three-dimensional tissue according to any one of <1> to <7>,
wherein the cells of the second type are cells that emit light by chemiluminescence, bioluminescence, or fluorescence in response to an external stimulus.
<10> The three-dimensional tissue according to <9>,
wherein a reporter gene is introduced into the cells of the second type.
<11> The three-dimensional tissue according to <9> or <10>,
wherein a reporter gene different from the reporter gene introduced into the cells of the first type is introduced into the cells of the second type.
<12> The three-dimensional tissue according to any one of <9> to <11>,
wherein the cells of the second type are physiologically different from the cells of the first type.
<13> The three-dimensional tissue according to any one of <1> to <12>, further including
one or more types of cells that are different from the cells of the first type and the cells of the second type.
<14> The three-dimensional tissue according to any one of <1> to <13>,
wherein the first cellular region is maintained at a position by a fixative.
<15> The three-dimensional tissue according to any one of <1> to <14>,
wherein the three-dimensional tissue is used for evaluation of safety of a substance, evaluation of efficacy of a substance, or screening of drugs.

The three-dimensional tissue according to any one of <1> to <15> can solve the various problems in the related art and can achieve the object of the present invention.

REFERENCE SIGNS LIST

10: three-dimensional tissue
11: region including cells A
12: region including cells B
13: medium
14: culture container
21: coagulation factor
41: culture
71: stimulating substance
81: bottom
M: micropipette
P: inkjet bioprinter

The invention claimed is:

1. A three-dimensional tissue, comprising:
a first cellular region that comprises cells of a first type; and
a second cellular region that comprises cells of a second type different from the first type,
wherein the cells of the first type comprise a reporter gene linked downstream of a promoter of a target gene that emits light in response to an external stimulus, wherein the light is emitted by chemiluminescence, bioluminescence, or fluorescence,
wherein the cells of the first type are absent in the second cellular region, and
wherein the three-dimensional tissue is formed by
dispensing a solution comprising collagen and the cells of the second type into a container and allowing the solution comprising collagen and the cells of the second type to solidify;
dispensing a solution comprising fibrinogen on the solidified solution comprising cells of the second type followed by dispensing a mixture of the cells of the first type and thrombin; and
subsequently dispensing an additional volume of the solution comprising collagen and the cells of the second type into the container, wherein the solution comprising collagen and the cells of the second type is allowed to solidify, and wherein the cells of the first type do not contact the container.

2. The three-dimensional tissue according to claim 1, wherein relatively to the total region comprising both the first cellular region and the second cellular region, the proportion of the first cellular region is smaller than the proportion of the second cellular region.

3. The three-dimensional tissue according to claim 1, wherein a surface of the first cellular region is present at a certain distance on an axis perpendicular to an interface to which a stimulus is applied to the three-dimensional tissue.

4. The three-dimensional tissue according to claim 1, wherein the first cellular region is not in contact with a circumferential wall of the container.

5. The three-dimensional tissue according to claim 1, wherein the cells of the second type are not cells that emit light.

6. The three-dimensional tissue according to claim 1, wherein the cells of the second type are cells that emit light by chemiluminescence, bioluminescence, or fluorescence in response to an external stimulus.

7. The three-dimensional tissue according to claim 6, wherein a reporter gene is introduced into the cells of the second type.

8. The three-dimensional tissue according to claim 6, wherein the reporter gene introduced into the cells of the second type is different from the reporter gene introduced into the cells of the first type.

9. The three-dimensional tissue according to claim 6, wherein the cells of the second type are physiologically different from the cells of the first type.

10. The three-dimensional tissue according to claim 1, further comprising:
one or more types of cells that are different from the cells of the first type and from the cells of the second type.

11. The three-dimensional tissue according to claim 1, wherein the three-dimensional tissue is used for evaluation of safety of a substance, evaluation of efficacy of a substance, or screening of drugs.

12. The three-dimensional tissue according to claim 1, wherein the cells of the first type are not in contact with a circumferential wall of a culture chamber comprising the three-dimensional tissue.

13. The three-dimensional tissue according to claim 1, wherein the cells of the first type are arranged in the center of the three dimensional tissue.

* * * * *